United States Patent
Kurihara

(10) Patent No.: US 8,317,769 B2
(45) Date of Patent: Nov. 27, 2012

(54) ABSORBING ARTICLE WITH FOLDED SIDE BARRIERS

(75) Inventor: Ryoko Kurihara, Sakura (JP)

(73) Assignee: Daio Paper Corporation, Shikokuchuo-shi (JP)

(*) Notice: Subject to any disclaimer, the term of this patent is extended or adjusted under 35 U.S.C. 154(b) by 262 days.

(21) Appl. No.: 12/448,571

(22) PCT Filed: Dec. 27, 2007

(86) PCT No.: PCT/JP2007/075110
§ 371 (c)(1),
(2), (4) Date: Jun. 25, 2009

(87) PCT Pub. No.: WO2008/081862
PCT Pub. Date: Jul. 10, 2008

(65) Prior Publication Data
US 2010/0057033 A1  Mar. 4, 2010

(30) Foreign Application Priority Data
Dec. 27, 2006 (JP) .................... 2006-351225

(51) Int. Cl.
*A61F 13/15* (2006.01)
*A61F 13/475* (2006.01)

(52) U.S. Cl. .................. 604/385.28; 604/385.24

(58) Field of Classification Search ............ 604/385.01, 604/385.03, 385.04, 385.22, 385.24–385.28
See application file for complete search history.

(56) References Cited

U.S. PATENT DOCUMENTS

| 4,904,251 | A | * | 2/1990 | Igaue et al. | 604/385.26 |
| 5,114,420 | A | * | 5/1992 | Igaue et al. | 604/385.26 |
| H1440 | H | * | 5/1995 | New et al. | 604/386 |
| 5,577,540 | A | * | 11/1996 | Sageser | 156/226 |
| 2002/0062116 | A1 | * | 5/2002 | Mizutani et al. | 604/385.28 |
| 2003/0040731 | A1 | * | 2/2003 | Nozaki et al. | 604/385.28 |
| 2004/0059311 | A1 | * | 3/2004 | Minato et al. | 604/385.27 |
| 2004/0181202 | A1 | * | 9/2004 | Corneliusson | 604/385.27 |

FOREIGN PATENT DOCUMENTS

| JP | 2908877 | 6/1999 |
| JP | 2000-189459 | 7/2000 |
| JP | 2002-165836 | 6/2002 |
| JP | 2003-62008 | 3/2003 |

* cited by examiner

*Primary Examiner* — Lynne Anderson
*Assistant Examiner* — Kathryn E Ditmer
(74) *Attorney, Agent, or Firm* — Jordan and Hamburg LLP

(57) ABSTRACT

A sanitary napkin comprises an absorbent interposed between a liquid-permeable surface sheet and a liquid-impermeable back sheet and enlarged to have a larger absorbent width on the back end than that of a crotch portion, and stereo gathers on the two sides of the surface. The stereo gathers have one or more folded-back portions formed at positions on the back end of the vicinity of a body liquid discharging portion, and the sanitary napkin is made to have a larger width between the stereo gathers on the back end thereof than that at the body liquid discharging portion.

4 Claims, 6 Drawing Sheets

FRONT END

BACK END

ABSORBING ARTICLE WITH FOLDED SIDE BARRIERS

BACKGROUND OF THE INVENTION

The present invention relates to an absorbing article for absorbing menses or vaginal discharges, such as a sanitary napkin, a panties liner or an incontinence pad.

In the prior art, the known absorbing article such as the sanitary napkin, the panties liner, the vaginal discharge sheet or the incontinence pad is prepared by interposing an absorbent such as cotton pulp between a liquid-impermeable back sheet such as a polyethylene sheet or a polyethylene laminated nonwoven fabric and a liquid-permeable surface sheet such as nonwoven fabric or a permeable plastic sheet.

The body liquid such as menses is generally absorbed by the abutting portion of the absorbent on a body liquid discharge port. The body liquid may diffuse, if once much discharged, along the surface of the napkin or may flow through the clearance, if formed from the skin, on the body so that it diffuses forward and backward or to the right and left of the napkin. These tendencies are intensified especially while the napkin wearer is sleeping, so that the body liquid diffuses widely to the back of the napkin. In the known night sanitary napkin, therefore, the absorbent is made wider on the back end than at the crotch portion (as referred to Patent Documents 1 and 2, for example).

On the other hand, the means for preventing the transverse leakage is frequently practiced by forming stereo gathers on the two sides of the surface side. These stereo gathers are usually formed linearly along the longitudinal direction of the product. However, there arises a problem that the absorbent portions on the outer sides of the stereo gathers do not function substantially in the back end portion, in case the stereo gathers are applied to the absorbing article, in which the absorbent width at least on the aforementioned back end is larger than that of the crotch.

In order to solve this problem, Patent Document 3 has proposed a paper diaper, as shown in FIG. 7, in which stereo gathers 60 are arranged such that their spacing is narrowed in the crotch portion but is gradually widened at the front end portion and the back end portion.

On the other hand, Patent Document 4 has proposed an absorbing article 70, as shown in FIG. 8, in which an absorbent is interposed between a liquid-permeable surface sheet and a liquid-impermeable back sheet, which is so curvilinearly formed that the absorbent width of at least the back-side rear end may be larger than that of the crotch, and which has stereo gathers 72 on the two sides of the surface. The stereo gathers 72 are provided, in the crotch region containing the body liquid discharging portion, with gather rising points 72*b* at positions close to the side edges of the absorbent 71, and are shaped to bulge inward, when expanded, substantially along the side edges of an absorbent 71 with reference to imaginary lines joining the longitudinal starting end portions 73 and the longitudinal terminating end portions 74 of the stereo gathers 72. These stereo gathers 72 are so constituted within their formed range as to have the gather rising points 72*b*, at which the sheet material forming the stereo gathers 72 is folded back outward along the gather longitudinal direction, and free ends 72*a* which are positioned on the outer sides of the gather rising points 72*b*.

Patent Document 1: JP-A-2000-189459
Patent Document 2: JP-A-2003-62008
Patent Document 3: Japanese Patent No. 2908877
Patent Document 4: JP-A-2002-165836

SUMMARY OF THE INVENTION

In the diaper described in Patent Document 3, however, the stereo gathers 60 rise along virtual lines 61 and 61 and substantially normal to the surface sheet face. At the front end and the back end, the gathers rises while being inclined inward. The stereo gathers having stood substantially vertically before worn may be felled down inward by the abutments on the skin, and the whole width of the absorbent may not be effectively exploited.

Moreover, the absorbing article described in Patent Document 4 requires a complicated manufacturing technique for arranging the stereo gathers curvilinearly in an arcuate shape, as viewed in a top plan, on a manufacturing line. This arrangement raises a problem that the manufacture is difficult and requires heavy investments for the facilities.

Preferably, a main object of the invention is to propose an absorbing article, in which an absorbent width on the back end is made larger than that of a crotch portion, and which includes stereo gathers on the two sides of the surface side, and a stereo gather structure in the absorbing article, in which an absorbent can be exploited on the back side as a wide effective absorbing face and which can be easily manufactured.

In order to solve the problems, according to a first aspect of the invention, there is provided an absorbing article comprising an absorbent interposed between a liquid-permeable surface sheet and a back sheet, and stereo gathers on the two sides of the surface, characterized in that the stereo gathers have one or more folded-back portions formed at positions on the back end of the vicinity of the body liquid discharging portion, and in that the absorbing article is made to have a larger width between the stereo gathers on the back end thereof than that at the body liquid discharging portion.

In the first aspect of the invention, the stereo gathers have one or more folded-back portions formed at positions on the back end of the vicinity of the body liquid discharging portion, and the width between the stereo gathers is made larger on the back end of the absorbing article than that at the liquid discharging portion. As a result, the absorbent can be exploited as a widely effective absorbing face on the back side of the absorbing article. Moreover, the stereo gathers are not curvilinearly folded but are folded back into the non-linear arrangement, so that they can be manufactured simply and easily.

In a second aspect of the invention, there is provided an absorbing article as set forth in claim 1, wherein the stereo gathers have an even number of folded-back portions, and wherein the inclination angle of the front end of the absorbing article in the top plan view is set equal to the inclination angle of the absorbing article at the back end in the top plan view.

According to the second aspect of the invention, the stereo gathers satisfy (1) the condition that they have an even number of folded-back portions, and (2) the condition that the inclination angle, as viewed in the top plan view, at the front end of the absorbing article is set equal to the inclination angle, as viewed in the top plan view, at the back end of the absorbing article. As a result, the nonwoven sheets or the like for forming the stereo gathers continuously can be arranged in the absorbing articles arrayed in series on the line so that the absorbing articles can be continuously manufactured.

In a third aspect of the invention, there is provided an absorbing article according to the first or second aspects of the invention, wherein the absorbent width on the back end is enlarged to become wider than that of the crotch portion.

The third aspect of invention is applied to the absorbing article, in which the absorbent width on the back end is enlarged to become wider than that of the crotch portion. In the invention, the effect is more prominent, if it is applied to an absorbing article, in which the absorbent width on the back end is made larger than that of the crotch portion, than if applied to the absorbing article having an absorbent of an equal width.

In a fourth aspect of the invention, there is provided an absorbing article according to the first or second aspect of the invention, wherein the absorbent width on the back end is enlarged to become wider than that of the crotch portion, and wherein the absorbent on the back end is divided into a central absorbent as wide as the absorbent in the crotch portion and side absorbents positioned on the two sides of the former.

In the fourth aspect of the invention, the absorbent having the relatively enlarged width on the back end is divided into the central absorbent as wide as the absorbent in the crotch portion and the side absorbents positioned on the two sides of the former. As a result, the side absorbents are pulled inward and curved by the tension of the stereo gathers so that they can follow the curves of the buttocks easily.

According to the invention, as has been described in detail hereinbefore, the absorbing article is formed such that the absorbent width on the back end is larger than the absorbent width on the crotch portion, and such that it is equipped with stereo gathers on the two sides on the surface side. The absorbent can be exploited on the back side as the wide effective absorbing face, and can be easily manufactured.

DETAILED DESCRIPTION OF THE INVENTION

First Mode of Embodiment

Figure 1:
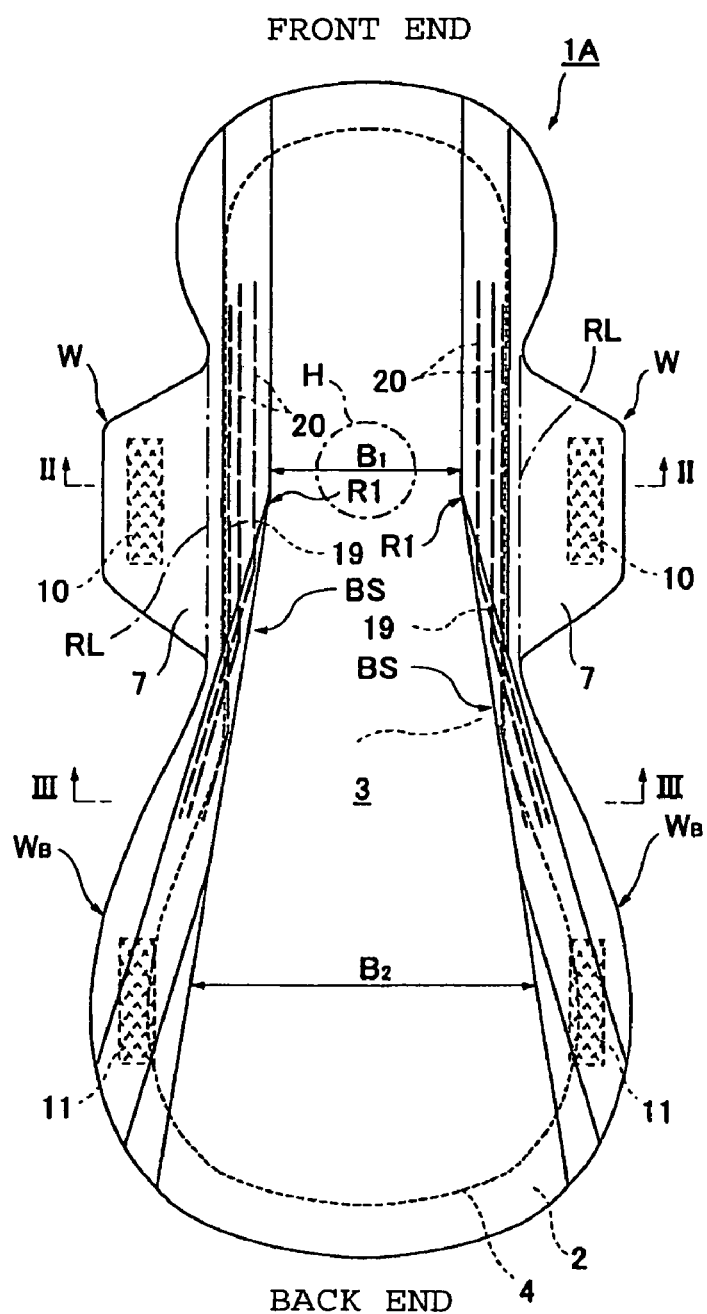
FIG. 1 is a development of a sanitary napkin 1A according to a first embodiment of the invention.
Figure 2:
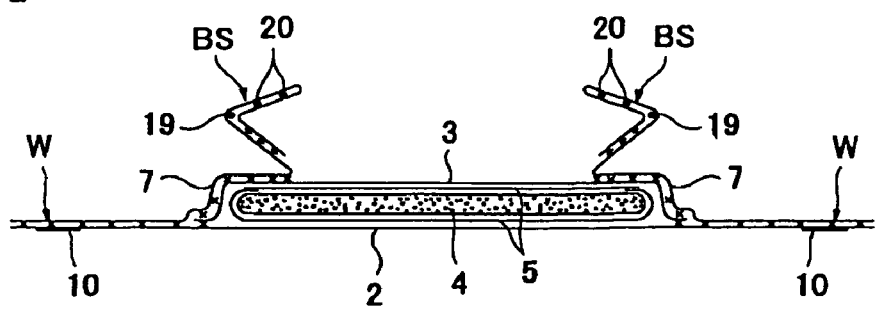
FIG. 2 is a view taken along line II-II of FIG. 1.
Figure 3:
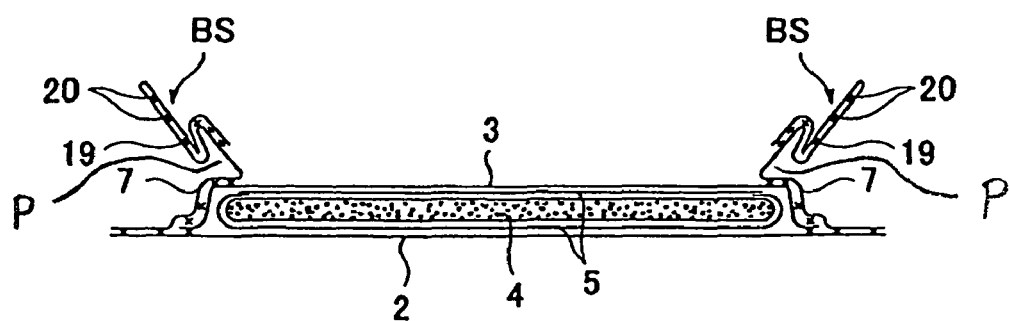
FIG. 3 is a view taken along line III-III of FIG. 1.

FIG. 1 is a development of a sanitary napkin 1; FIG. 2 is a view taken along line II-II of FIG. 1; and FIG. 3 is a view taken along line III-III of FIG. 1.

The sanitary napkin 1 is the so-called night napkin, which is constituted mainly of a liquid-impermeable back sheet 2 made of a polyethylene sheet or the like, a liquid-permeable surface sheet 3 for causing menses and vaginal discharges to permeate quickly therethrough, an absorbent 4 sandwiched between those two sheets 2 and 3 and made of cotton-like pulp, synthetic pulp or the like, a crepe paper 5 enclosing the absorbent 4 so as to keep the shape of and improve the diffusivity of the absorbent 4, and a pair of left and right stereo gathers BS and BS formed to protrude to the surface side in a predetermined longitudinal section containing at least a body liquid discharging portion H. Around the absorbent 4 and at its upper and lower end edges, moreover, the outer edge portions of the liquid-impermeable back sheet 2 and the liquid-permeable surface sheet 3 are joined by an adhesive such as a hot-melt or adhering means such as a heat seal. At the two side edge portions, moreover, the liquid-impermeable back sheet 2 extending sideways of the absorbent 4 and side nonwoven fabrics 7 forming the stereo gathers BS are joined by an adhesive such as a hot melt or adhering means such as a hot seal. Sideways protruding wing-shaped flaps W and W are formed of the laminated sheet portions of those liquid-impermeable back sheet 2 and the side nonwoven fabrics 7. Second wing-shaped flaps $W_B$ and $W_B$ are formed at the portions positioned closer to the buttock sides.

The structure of the sanitary napkin 1 is described in more detail in the following.

A sheet material having at least a water-barrier property, such as polyethylene is used for the liquid-impermeable back sheet 2. In recent years, however, there is a tendency that a moisture-permeable material is suitably used from the standpoint of preventing stuffiness. This water-barrier/moisture-permeable sheet material is properly exemplified by the finely porous sheet which is obtained by melting and kneading an inorganic filler in an olefin-group resin such as polyethylene or polypropylene thereby to form a sheet and then by elongating the sheet in one- or two-axis directions. On the unused face side (or the outer face) of the liquid-impermeable back sheet 2, there are formed body displacement stopping pressure-sensitive adhesive layers (not shown) of one or more stripes, which fix the sanitary napkin 1 on the shorts when the napkin 1 is worn on the body. The liquid-impermeable back sheet 2 may be made of a poly-laminated nonwoven fabric by laminating the plastic film and the nonwoven fabric.

The liquid-permeable surface sheet 3 is properly exemplified by a porous or non-porous nonwoven fabric, a porous plastic sheet or the like. The material fibers constituting the nonwoven fabric can be not only synthetic fibers such as an olefin group, e.g., polyethylene or polypropylene, a polyester group or a polyamide group but also reproduced fibers such as rayon or cupra, or natural fibers such as cotton. It is also possible to use the nonwoven fabric which is obtained by a suitable working method such as a spun lacing method, a spun bonding method, a thermal bonding method, a melt-blown method or a needle punching method. Of these working methods: the spun lacing method is excellent in softness; the spunbonding method is excellent in the richness of drapability; and the thermal bonding method and the air-through method are excellent in bulkiness and softness. The liquid-permeable surface sheet 3, when a plurality of pores are formed thereon, can absorb the menses, vaginal or the like discharge (as will be called together as the body liquid) quickly so that it is excellent in the dry touch.

The absorbent 4 can be exemplified by mixing a highly water-absorptive resin into the pulp or by mixing not only chemical fibers but also the highly water-absorptive resin into the pulp. As shown, each absorbent 4 is desirably enclosed by the crepe paper 5 so as to keep the shape, to diffuse the menses or the like quickly and to prevent the backflow of the menses or the like once absorbed. This pulp is exemplified by cellulose fibers such as chemical pulp or molten pulp made of wood, or artificial cellulose fibers such as rayon or acetate, and soft-wood pulp having longer fibers than those of hardwood pulp is used preferably for functions and prices.

The highly water-absorptive resin can be exemplified by crosslinked polyacrylate, self-crosslinked polyacrylate, saponified, crosslinked copolymer of acrylic ester-vinyl acetate, crosslinked copolymer of isobutylene-maleic anhydride, polysulphone acid base crosslinked material or partially crosslinked water-swelling polymer such as polyethylene oxide or polyacrylic amide. Of these, the preferred one is the acrylic acid or acrylate group which is excellent in the water absorption and the water absorbing rate. The highly water-absorptive resin having the water-absorbing performance can be adjusted in the water absorptivity and the water absorbing rate in its manufacturing process by adjusting the crosslinking density and the crosslinking density gradient. It is desired that the content of the highly water-absorptive resin is 10 to 60%. A sufficient absorptivity cannot be provided in case the content of the highly water-absorptive resin is less than 10%. In case the content is more than 60%, the pulp fibers are not entangled so that the sheet strength easily drops to cause tears, cracks or the like.

The absorbent 4 has a top plan formed generally into a guitar shape, in which the front end has an equal width and in which the absorbent width on the back side is made larger than the absorbent width in the crotch portion.

In the shown example, on the other hand, the width size of the liquid-permeable surface sheet 3 is made so slightly larger than the width of the absorbent 4, as shown in the transverse sections of FIG. 2 and FIG. 3, as to cover only the absorbent 4. The stereo gathers BS are constituted of the side nonwoven fabrics 7 different from the liquid-permeable surface sheet 3, such as the nonwoven fabric material which has been subjected to a suitable water-repelling treatment or a hydrophilic treatment in accordance with the object to prevent the penetration of menses, vaginal discharge or the like or to enhance the texture. Those side nonwoven fabrics 7 to be used can be formed by subjecting the material of natural fibers, synthetic fibers, reproduced fibers or the like to a suitable processing method. In order to eliminate the stiffness and to prevent the stuffiness, it is advisable to use the nonwoven fabric which is made air-permeable by suppressing a basis weight. Specifically, it is desirable to use the nonwoven fabric which has been manufactured to have the basis weight of 15 to 23 g/m2. The permeation of the body liquid is reliably prevented by using the nonwoven fabric which has been treated with coating the water-repellent or the like of a silicone group, a paraffin group or an alkylchromic chloride group.

As shown in FIG. 2 and FIG. 3, the side nonwoven fabrics 7 are adhered by means of an adhesive such as the hot melt at their portions on the outer side of the widthwise intermediate portion over the range from the inner side positions of the absorbent 4 to the outer edges of the liquid-impermeable back sheet 2 slightly across the absorbent side edges. A pair of left and right wing-shaped flaps W and W are formed of the laminated sheet portions of those side nonwoven fabrics 7 and liquid-impermeable back sheet 2 at the absorbent side positions corresponding substantially to the body liquid discharging portion. Second wing-shaped flaps $W_B$ and $W_B$ are formed at the portions positioned closer to the buttock sides. On the outer faces of those wing-shaped flaps W and W and second wing-shaped flaps $W_B$ and $W_B$, respectively, there are disposed pressure-sensitive adhesive layers 10 and so on and 11 and so on. When the sanitary napkin is worn with respect to the shorts, the wing-shaped flaps W and W are folded back at the positions near fold-back lines RL so that the sanitary napkin is fixed by winding the wing-shaped flaps W and W on the crotch portion of the shorts.

First Embodiment of Stereo Gathers BS

The inner portions of the side nonwoven fabrics 7 are folded substantially doubly, and filament-like elastically extensible members 19 are so arranged in the double sheets that they are fixed at two ends or at longitudinally suitable positions in the intermediate portions of the height direction. A plurality of or two filament-like elastically extensible members 20 and 20 are so arranged in the shown embodiment that they are fixed at two ends or at suitable longitudinal positions. These double sheet portions are so adhered at their front end to the sides of the absorbents 4 that they are folded and laminated in the Z-shaped section. In the region near the body liquid discharging portion H, the stereo gathers BS and BS rising from the surface side are formed such that pockets P and P are opened inward in bent sections at the portions arranging the filament-like elastically extensible members 19.

The stereo gathers BS have one or more, e.g., one folded-back portion R1 formed, in the embodiment of FIG. 1, at a position on the back end of the vicinity of the body liquid discharging portion H, and the sanitary napkin 1A is made to have a larger width B2 between the stereo gathers BS and BS on the back end thereof than a width B1 between the stereo gathers BS and BS of the body liquid discharging portion H. In the embodiment shown in FIG. 1, the stereo gathers BS are folded back outward only once, and are adhered such that they are gradually enlarged from the starting points along the side (inner) edges of the absorbent 4. As a result, the width B2 between the stereo gathers BS and BS is gradually enlarged toward the back end.

The stereo gathers BS are desirably formed into a Z-shaped sectional structure having a bent section. At the front end of the sanitary napkin 1A, the surface side is raised to the surface side while forming the pockets P and P to have inward openings, so that it keeps a sufficient height and dams up the body liquid. At the back end of the sanitary napkin 1A folded back outward, as shown in FIG. 3, the partitions of a double structure are easily formed to enhance the body liquid damming effect.

Second Embodiment of Stereo Gathers BS

Figure 4:
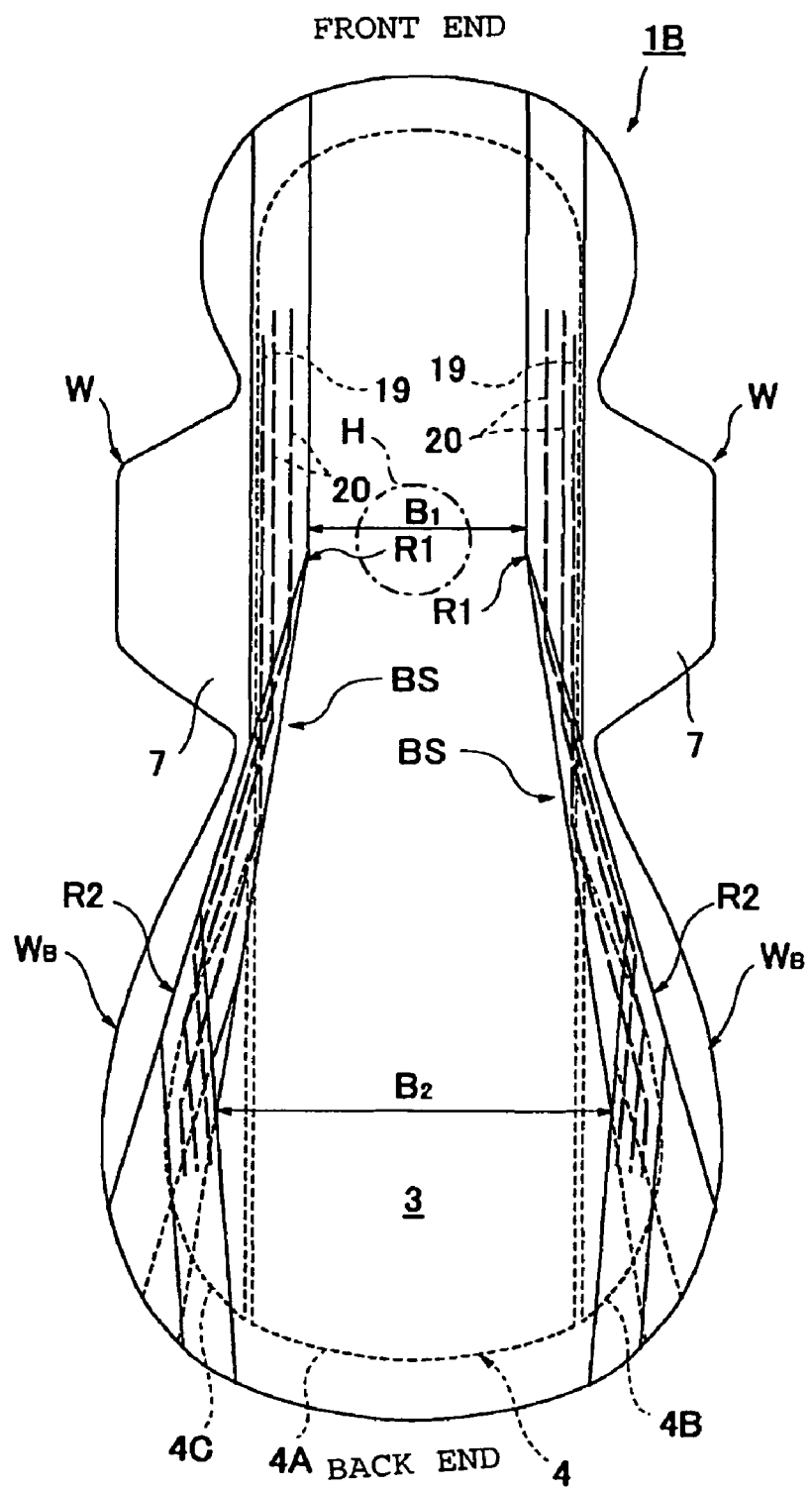
FIG. 4 is a development of a sanitary napkin 1B according to a second embodiment of the invention.

Next, a sanitary napkin 1B shown in FIG. 4 exemplifies the structure of the stereo gathers BS according to the second embodiment.

The stereo gathers BS have two folded-back portions R1 and R2 formed at positions on the back ends closer to the body liquid discharging portion H, and the sanitary napkin 1B is made to have a width B2 larger between the stereo gathers BS and BS on the back end thereof than a width B1 between the stereo gathers BS and BS. In the embodiment shown in FIG. 4, the stereo gathers BS are at first folded back outward, and are adhered such that they are gradually enlarged from the starting points along the side (inner) edges of the absorbent 4. Then, the stereo gathers BS are folded back inward on the back side, and are adhered to the surface sheet 3.

In the worn state or stereo state, the rising portions of the stereo gathers BS are unclear at the folds of the folded-back portions R1 and R2. However, the rising points are shifted to the outer side on the back end than on the front end, so that the stereo gathers BS rise to draw gentle S-shaped curves in a top plan view.

In the embodiment shown in FIG. 4, the absorbent width on the back end is enlarged more than that in the crotch portion, and the absorbent on the back end is divided into a central absorbent 4A as wide as the absorbent in the crotch portion and side absorbents 4B and 4C positioned on the two sides of the former. The side absorbents 4A and 4B are pulled inward and curved by the tension of the stereo gathers BS so that they can follow the curves of the buttocks easily.

Third Embodiment of Stereo Gathers BS

Figure 5:
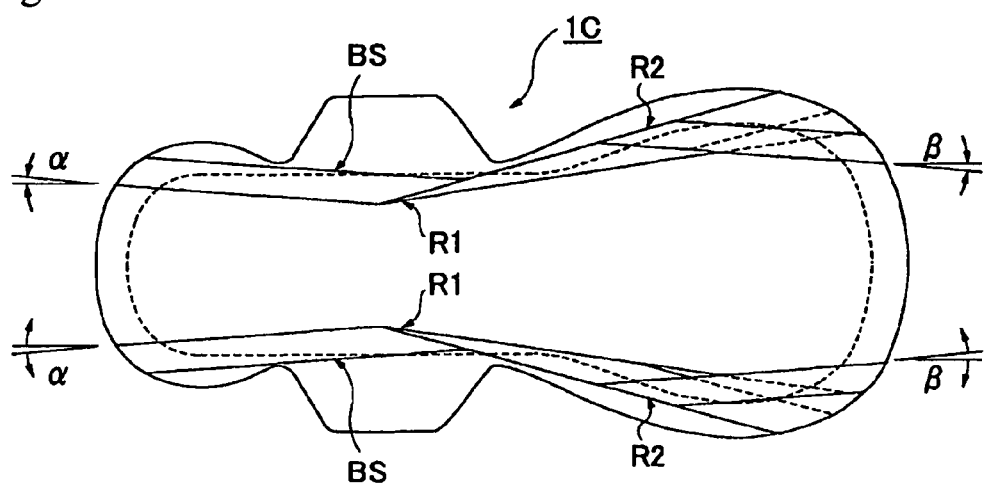
FIG. 5 is a development of a sanitary napkin 1C according to a third embodiment of the invention.

Moreover, a sanitary napkin 1C shown in FIG. 5 exemplifies the structure of the stereo gathers BS according to the third embodiment.

Figure 6:
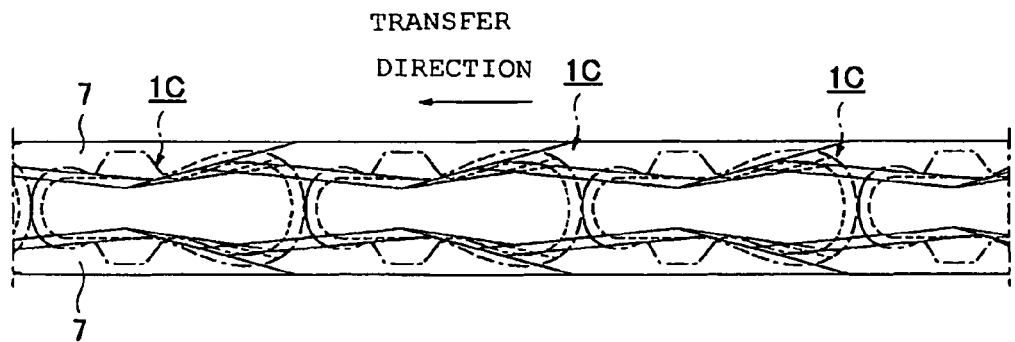
FIG. 6 is a line top plan view showing the manufacturing procedure of the sanitary napkin 1C.
Figure 7:
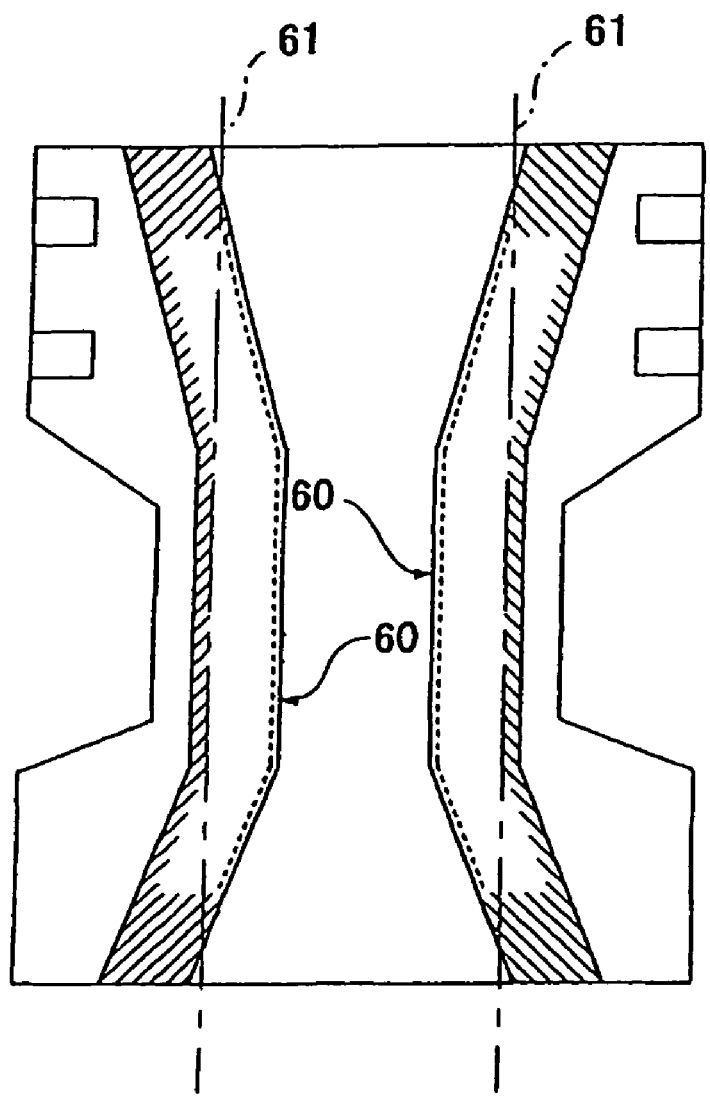
FIG. 7 is a top plan view of the absorbing article (1) of the prior art.
Figure 8:
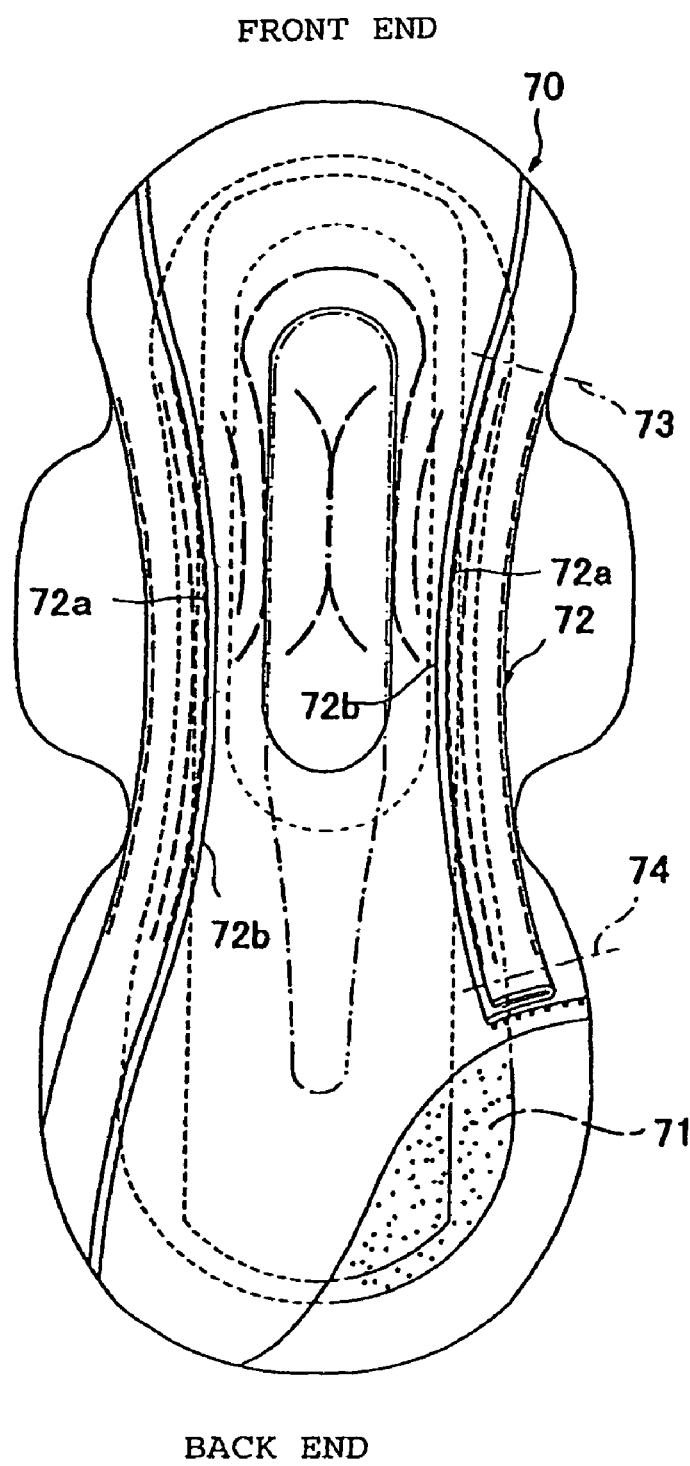
FIG. 8 is a top plan view of the absorbing article (2) of the prior art.

In this embodiment, like the aforementioned second embodiment, the stereo gathers BS have the two folded-back portions R1 and R2 formed at positions on the back ends closer to the body liquid discharging portion H, and the width B2 between the stereo gathers BS and BS of the body liquid discharging portion H is made larger than the width B1 between the stereo gathers BS and BS. However, the inclination angle α of the stereo gathers BS, as viewed in the top plan view, at the front end of the sanitary napkin 1C is set equal to the inclination angle β of the stereo gathers BS, as viewed in the top plan view, at the back end. As a result, the side nonwoven fabrics 7 for forming the stereo gathers continuously can be arranged in the sanitary napkins 1C arrayed in series on a manufacturing line, as shown in FIG. 6, so that the sanitary napkins 1C can be continuously manufactured.

Here, the folding-back number of the stereo gathers BS is made to form the two folded-back portions R1 and R2 in this embodiment, but may be even.

Other Embodiments (1) In the foregoing embodiments, the absorbent 4 is formed such that the absorbent width on the back end is enlarged to become wider than that of the crotch portion. However, the invention can also be applied to an absorbing article having the absorbent which has an equal width all over the length.
(2) In the foregoing embodiments, the folding number of the stereo gathers BS is one or two. However, the folding number may be an arbitrary one such as three or four.

The invention claimed is:

1. An absorbing article for wear by a person, comprising an absorbent interposed between a liquid-permeable surface sheet and a back sheet, each sheet being adhesively joined to each other so as to sandwich the absorbent therebetween, and, relative to a longitudinal axis of the absorbing article, Z-shaped stereo gathers that extend a length on two lateral sides of a body-facing surface of the liquid-permeable surface sheet that comprise nonwoven fabric foldably layered into a Z-shape along the entire length of said stereo gathers when viewed in cross-section,
    wherein said Z-shaped stereo gathers are affixed to said back sheet and have first folded-back portions in which a respective folded-back portion extends from the vicinity of a body liquid discharging portion of the person toward a back end of the article and upwardly relative to the body-facing surface,
    and wherein a width between the stereo gathers on the lateral two sides, as measured from where the folded-back portions begin to upwardly extend from the body-facing surface, increases toward the back end of the absorbing article, and the absorbing article has a larger width between the stereo gathers on the back end of the absorbing article than the width at the body liquid discharging portion.

2. An absorbing article as set forth in claim 1, wherein said stereo gathers have second folded-back portions positioned rearward of said first folded-back portions relative to the longitudinal axis of the absorbent article so that the absorbent article comprises an even number of folded-back portions providing for successive outward and inward folds of the stereo gathers relative to the longitudinal axis of the absorbent article, and wherein an inclination angle of the stereo gathers at a front end of the article in a top plan view is set equal to an inclination angle of the stereo gathers at the back end in the top plan view.

3. An absorbing article as set forth in claim 1 or 2, wherein width of the absorbent on the back end of the absorbing article is greater than at a crotch portion thereof.

4. An absorbing article as set forth in claim 3, wherein the absorbent on said back end is divided into a central absorbent as wide as the absorbent in the crotch portion and side absorbents positioned on two lateral sides of the central absorbent.

* * * * *